United States Patent [19]

Robins

[11] Patent Number: 5,283,197

[45] Date of Patent: Feb. 1, 1994

[54] METHOD OF MONITORING COLLAGEN DEGRADATION

[75] Inventor: Simon P. Robins, Aberdeen, Scotland

[73] Assignee: The Rowett Research Institute, Scotland

[21] Appl. No.: 17,333

[22] PCT Filed: Jun. 26, 1989

[86] PCT No.: PCT/GB89/00715

§ 371 Date: Jan. 23, 1991

§ 102(e) Date: Jan. 23, 1991

[87] PCT Pub. No.: WO89/12824

PCT Pub. Date: Dec. 28, 1989

Related U.S. Application Data

[63] Continuation of Ser. No. 623,792, Jan. 23, 1991, abandoned.

[30] Foreign Application Priority Data

Jun. 25, 1988 [GB] United Kingdom ................ 8815174

[51] Int. Cl.$^5$ ..................... G01N 33/493; C07K 3/02; C07K 13/00

[52] U.S. Cl. .................... 436/87; 530/356; 436/86

[58] Field of Search .................... 436/87, 86; 530/356

[56] References Cited

U.S. PATENT DOCUMENTS 4,973,666 11/1990 Eyre .................... 530/323

OTHER PUBLICATIONS

Eyre, D., et al., "Identification of Urinary Peptides Derived From Cross-Linking Sites in Bone Collagen in Paget's Disease, " Abstract No. 565 from *Jounral of Bone and Mineral Research* Jun. 4–7:S210 (1988).
Fujimoto, D., et al., "Analysis of Pyridinoline, a Cross-Linking Compound of Collagen Fibers, in Human Urine," *J. Biochem.* 94:1133–1136 (1983).
Robins, S. P., Biochem J. 215, 167–173 (1983).
Pinnell, S., Biochim. Biophys. Acta 229, 119–122 (1971).

*Primary Examiner*—Christine M. Nucker
*Assistant Examiner*—M. P. Woodward
*Attorney, Agent, or Firm*—Peter J. Dehlinger; Vincent M. Powers

[57] ABSTRACT

A method of monitoring collagen degradation, comprising assaying a biological fluid sample which contains a fragment of collagen including lysyl pyridinoline or hydroxylysyl pyridinoline or a substituted form thereof, a method of determining the tissue origin or degraded collagen thereby.

3 Claims, No Drawings

METHOD OF MONITORING COLLAGEN DEGRADATION

This application is a continuation of application Ser. No. 07/624,792, filed Jan. 23, 1991, now abandoned.

This invention relates to a method of monitoring collagen degradation as a diagnostic aid in relation particularly to osteoporosis and rheumatoid arthritis.

Collagen is present in various form in all tissue. It has been shown (Fujimoto et al., (1978) Biochemistry, Biophysics Research Communication vol. 84, 52-57) that collagen has the form of amino acid chains cross-linked by pyridinoline. The pyridinium crosslinks are formed from three hydroxylysine residues, two from the terminal (non-helical) peptides of the collagen molecule that are enzymatically converted to aldehydes before reaction and a third hydroxylysine situated in the helical portion of a neighbouring collagen molecule. Robins et al (Annals of the Rheumatic Diseases 1986, 45, 969-973) have described a technique for measurement of pyridinoline in urine by use of an antibody specific to pyridinoline and detected by enzyme-linked immunosorbent assay (ELISA). This technique, however gives a measure only of hydroxylysyl pyridinoline in the sample, and does not recognise lysyl deoxypyridinoline. The former is present in bone and tissue, and the latter in bone only. Thus the technique may indicate the occurrence of collagen degradation, indicating the presence of degenerative disease, but without indicating the type of tissue concerned.

The present invention is based on the recognition that lysyl and hydroxylysyl pyridinoline are present in biological fluid such as urine, attached to fragments of the original amino acid chains, or to sugars. However, there is no certainty as to where the original chains will have broken. In virtually all cases, however, sufficient amino acids will be present to identify the type of tissue from which the particular collagen derived.

Accordingly, the present invention provides a method of monitoring collagen degradation, comprising assaying a biological fluid sample which contains a fragment of collagen including lysyl pyridinoline or hydroxylysyl pyridinoline or a substituted form thereof.

Further according to the present invention there is provided a method of determining the tissue origin of degraded collagen, comprising assaying a biological fluid sample to determine the amount of lysyl pyridinoline or hydroxylysyl pyridinoline containing at least one substituents specific for the origin of the collagen degraded.

From another aspect, the invention resides in an antibody, preferably monoclonal, which is specific to a fragment of collagen which fragment comprises lysyl or hydroxylysyl pyridinoline having at least one amino acid attached thereto.

From another aspect, the invention resides in an antibody, preferably monoclonal, which is specific to a fragment of collagen which fragment comprises hydroxylysyl pyridinoline having a sugar residue attached thereto.

Preferably the pyridinoline is substituted with sections of original amino acid chains.

Preferably, said short sections of amino acid chains each comprise from one to five amino acids.

Preferably the sugar is linked to pyridinoline by glycosylation with galactose or with glucose and galactose.

The collagen may suitably be associated with one or cartilage.

Embodiments of the invention will now be described in further detail by way of example.

Collagen has the general structure:

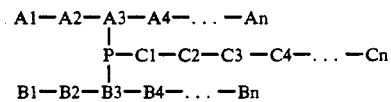

where A's, B's and C's are amino acids and P is lysyl or hydroxylysyl pyridinoline or glycosylated hydroxylysyl pyridinoline. When present in biological fluid, for example, urine, the A, B and C chains are broken and of indeterminate length. The invention is based on the fact that collagen from a specific body tissue will give rise in the biological fluid sample to the presence of

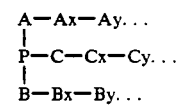

where A, B and C are short chains of from one to five amino acids, A, B, and C always being present, and Ax, Ay, Bx, By, Cx, Cy etc. are further parts of the original chains which may or may not be present. Further, A, B and C are specific to a particular tissue of origin. Therefore, this aspect of the invention operates on the unit

In another aspect of the invention X may be a glycosylated hydroxylysyl pyridinoline which may or may not have amino acids attached.

Hydroxylysine residues in the helix are glycosylated by addition of sugar groups at their hydroxyl group. Where formation of the pyridinoline (Pyd) crosslink involves a glycosylated hydroxylysine, a glycosylated crosslink will be produced. The crosslink analogue, lysyl-pyridinoline, formed by reaction with a lysine residue in the helix cannot form any glycosylated derivatives as it lacks the side-chain hydroxyl group.

There are two types of glycosylation, either galactose (Gal) alone or the disaccharide, glucosyl-galactose (Gal.Glc). Thus, there are two possible forms of glycosylated hydroxylysyl pyridinoline as shown below, Pyd-Gal and Pyd-Gal.Glc.

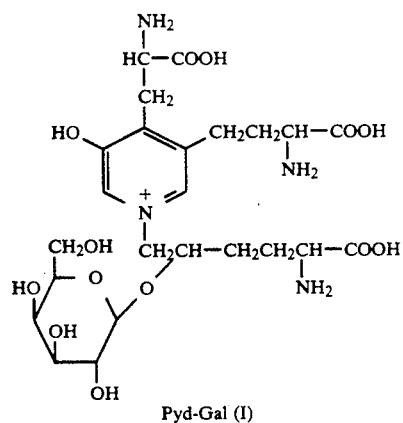

Pyd-Gal (I)

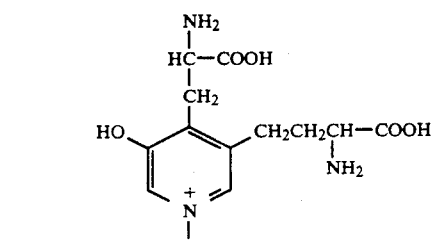

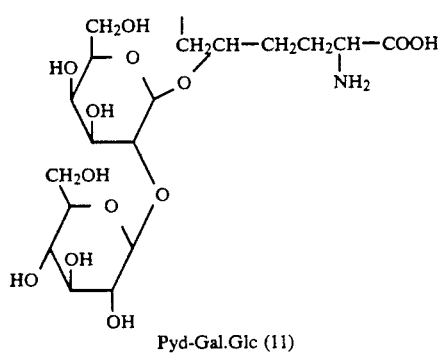

Pyd-Gal.Glc (II)

The relative proportion of mono- to di-saccharide derivatives of hydroxylysine varies with different tissues. For the main tissues of interest (i.e. those that contain pyridinoline) cartilage contains almost entirely Gal.Glc, whereas in bone collagen the monosaccharide predominates.

Both the mono- and di-saccharide derivatives of pyridinoline (structures I and II) have been isolated from human urine and identified. These components are present normally in urine but have been shown to be present in increased amounts in various bone disorders and in arthritic disease.

The main points of interest in these findings are:
1. The components are present in urine without hydrolytic treatment and an assay procedure would therefore be applicable directly to urine.
2. Assays of the two components will give some tissue-specific information on collagen breakdown. Measurement of Pyd-Gal will provide an index of bone collagen resorption: Pyd-Gal.Glc amounts in urine are primarily indicative of bone or cartilage degradation, and the relative amounts of Pyd-Gal and Pyd-Gal.Glc will provide information on the relative extent of bone and cartilage degradation.
3. The presence of the sugar groups may increase the antigenicity (ease with which good antibodies can be raised) of the components. The sugar portions will form part of the antibody recognition sites so that antibodies specific for each structure can be produced.

Two types of tissue of particular interest are bone and cartilage. The presence of degradation of bone collagen alone is an indicator of osteoporosis and other bone disorders, while the presence of degradation of both bone collagen and cartilage collagen is an indicator of arthritic disorders or diseases.

In general, the invention can be carried out by following the steps:
1. Identify a particular X of interest in biological fluid.
2. Isolate X.
3. Attach X to a suitable protein.
4. Inject the product of 3 into a host animal and raise antibody.
5. Use this antibody in ELISA or other suitable assay technique.

More specific examples of the invention will now be given.

Schemes 1 and 2 summarise the strategies for isolating crosslink-containing fragments from urine and give details of the components being isolated. Variations on these Schemes are detailed below.

EXAMPLE 1

Method a. Urine samples containing high concentrations of total pyridinium crosslinks were collected from patients with disorders involving either increased bone turnover (hyperparathyroidism) or increased cartilage and bone degradation (rheumatoid arthritis).

b. A total of 1.0–1.5l of urine was freeze-dried, redissolved in 0.2 M acetic acid and was subjected to gel filtration chromatography in batches using a 2.6×140cm column of Biogel P2.

c. Selected fractions containing pyridinium crosslink derivatives were re-chromatographed by reversed-phase HPLC using a $C_{18}$ support and elution with a mobile phase containing acetonitrile. The peptides were further purified by ion-exchange HPLC using DEAE- and SP-5PW columns.

d. The isolated components were characterized by fast atom bombardment mass spectrometry and amino acid sequence analysis; glycosylation sites were identified by gas-liquid chromatography of alkali hydrolysates of the peptides.

e. With a knowledge of the amino acid sequences around the crosslink sites in bone and cartilage, the tissues of origin of the peptides isolated from urine were established. A number of three peptides containing the core sequence representative of different tissues was chosen for raising antibodies.

f. Each of the purified peptides (1 μmol) were covalently attached to ovalbumin (0.25 μmol) using N-ethyl-N'-(3-dimethylaminopropyl) carbodiimide hydrochloride.

g. Balb/c mice were immunized with the ovalbumin conjugates and monoclonal antibodies were produced after fusion with Ag8.653 myeloma cells. Positive clones were detected by ELISA using microtube plates coated with the peptides attached to gelatin by reaction with a different carbodiimide reagent N-cyclohexyl-N'-2-(4'-methylmorpholinium) ethyl carbodiimide-p-toluene sulphonate.

The monoclonal antibodies so produced may be used in immunoassay tests for the diagnosis and monitoring of various types of bone disorders and degenerative joint diseases.

Example 2

Method

Step 1. Urine (300ml), concentrated to one tenth its original volume, was chromatographed on a column (3.0×100cm) of sephadex G25M with 0.2M-acetic acid as eluant. The fractions between 540 and 630ml ($V_e/V_o$=1.6-1.9) that contained approx. 60% of the characteristic pyridinium crosslink fluorescence were pooled and freeze-dried.

Step 2. The fraction from Step 1 (280mg) was re-chromatographed on a column (1.7×140cm) of Sephadex G10 eluted with 0.2M-acetic acid to separate the crosslinking components from amino acids and other small-M material. The fractions were monitored by fluorescence (Ex 295nm; Emm 400nm) and material that eluted between 105 and 121ml ($V_e/V_o$=1.1-1.3) was pooled and evaporated to dryness.

Step 3. The fraction from Step 2 was subject to cation-exchange chromatography on a column (0.9×15cm) of sulphonated polystyrene resin beads (5μ) cross-linked (8%) with divinyl benzene (Locarte Co Ltd, London; Cat No LA 48/08) run at 56 C and eluted with 67mM sodium citrate buffer, pH 3.84. Fractions of 5ml were collected and appropriate fractions were desalted on a column (1.7×50cm) of Sephadex GIO and freeze-dried.

In this system, Pyd-Gal (I) eluted between 91 and 105min and pyd-Gal.Glc (II) eluted between 41 and 50min.

Final purification of I and II was reversed-phase HPLC on a column (0.9×25cm) of Rosil $C_{18}$ packing (3μ), eluted with 0.1% heptafluorobutyric acid and a linear gradient from 15 to 30% acetonitrile over 30 min. (I) and (II) eluted at 17.3 and 16.9min respectively.

CHARACTERISATION

1. Hydrolysis characteristics

Mild acid hydrolysis (0.1 M HCI at 108 C for 12h) converted Pyd-Gal.Glc (II) completely into a mixture of Pyd-Gal (I) and pyridinoline (Pyd). Hydrolysis of Pyd-Gal (I) in 2M HCl at 108 C for 8h effected complete conversion of this component to Pyd. This behaviour is characteristic for these types of compound and has been noted previously for the interconversion of hydroxylysine glycosides to hydroxylysine.

2. Composition

On hydrolysis with strong mineral acid, both compounds (I) and (II) produced Pyd with no other amino acids detected in the hydrolysates. The carbohydrate compositions were determined by gas-liquid chromatography of methylated derivatives, after hydrolysis in 2M $H_2SO_4$ and reduction with sodium borohydride Based on these results and determination of the amounts of crosslink by HPLC, the molar ratios were:

Component I Pyridinoline (1.0); Galactose (0.9)
Component II Pyridinoline (1.0): Galactose (0.8); Glucose (0.9)

The results above therefore confirm that the structures of compounds I and II are as shown earlier.

In addition to the above, an associated derivative, termed 'X', that eluted between 184 and 195min at Step 3, has been isolated. This component contains Pyd and is increased in amount in patients with bone disorders.

Immunoassays for these components will be developed precisely as described for the peptides by conjugation to ovalbumin through their amino or carboxyl groups.

Modification and improvements may be incorporated without departing from the scope of the invention.

SCHEME 1

URINE
Concentrated to one tenth vol.
↓
STEP 1
Gel Filtration on Sephadex-G25M
↓
STEP 2
Small components fractionated by gel filtration on Sephadex-G10
↓
STEP 3
Separation and purification by ion-exchange chromatography and HPLC
Characterisation of glycosylated derivatives:
Pyd.Gal.Glc (I), Pyd.Gal (II)

SCHEME 2

URINE
Concentrated to one tenth vol.
↓
STEP 1
Gel Filtration on Sephadex-G25M
↓
STEP 2
Larger Components fractionated by gel filtration on Biogel-P6
↓
STEP 3
Reversed-phase HPLC with TFA/acetonitrile Isolation of three crosslinked peptide components (III, IV & V) with retention times of 27.2, 31.7 and 36.2 min respectively
↓
STEP 4
Purification of IV and V by HPLC with HFBA/acetonitrile
↓
STEP 5
Purification of III by ion-exchange chromatography on a DEAE-5PW column and by further HPLC (as step 4)

I claim:

1. A method of monitoring bone collagen degradation in a human subject comprising:

obtaining a urine sample from the subject, chromatographically separating glycosylated, peptide-free hydroxylysyl pyridinolines in the urine sample wherein said sample is not hydrolyzed and, determining the amount of a glycosylated, peptide-free hydroxylysyl pyridinoline as an indicator of bone collagen degradation.

2. The method of claim 1, wherein the glycosylated, peptide-free hydroxylysyl pyridinoline is galactosyl-pyridinoline.

3. The method of claim 1, wherein the glycosylated, peptide-free hydroxylysyl pyridinoline is glucosyl-galactosyl-pyridinoline.

* * * * *

UNITED STATES PATENT AND TRADEMARK OFFICE
CERTIFICATE OF CORRECTION

PATENT NO. : 5,283,197
DATED : Feb. 1, 1994
INVENTOR(S) : Simon P. Robins

It is certified that error appears in the above-identified patent and that said Letters Patent is hereby corrected as shown below:

Col. 1, line 10, "form" should be --forms--.

Col. 1, line 11, "Biochemistry" should be --Biochemical-

Col. 1, line 26, "deoxypyridinoline" should be --pyridinoline--.

Col. 1, line 50, "substituents" should be --substituent--.

Col. 2, line 1, "one" should be --bone--.

Col. 3, in the structure spanning lines 18-40, the bond leading downward from the positively charged nitrogen (line 25) should be connected to the bond leading upward from the $CH_2$ group at line 29.

Col. 3, line 40, "Pyd-Gal.Glc(11)" should be --Pyd-Gal.Glc(II)--.

Col. 4, line 53, "A number of three" should be --Three--.

Col. 5, line 27, "56 C" should be --56°C--.

Col. 5, line 30, "GIO" should be --G10--.

Col. 5, at about line 35, --accomplished by-- should be inserted after "was".

Col. 5, line 44, "108 C" should be --108°C--.

UNITED STATES PATENT AND TRADEMARK OFFICE
CERTIFICATE OF CORRECTION

PATENT NO. : 5,283,197
DATED : Feb. 1, 1994
INVENTOR(S) : Simon P. Robins

It is certified that error appears in the above-indentified patent and that said Letters Patent is hereby corrected as shown below:

Col. 5, line 47, "108 C" should be --108°C--, and "HCI" should be --HCl--.

Col. 6, line 30, "Pyd.Gal.Glc. (I), Pyd.Gal (II)" should be --Pyd.Gal (I), Pyd.Gal.Glc. (II)--.

Signed and Sealed this

Eleventh Day of April, 1995

Attest:

BRUCE LEHMAN

Attesting Officer

Commissioner of Patents and Trademarks